United States Patent
Oh (10) Patent No.: US 10,143,440 B2
(45) Date of Patent: Dec. 4, 2018

(54) ULTRASONIC IMAGING DEVICE

(71) Applicant: SAMSUNG ELECTRONICS CO., LTD., Suwon-si, Gyeonggi-do (KR)

(72) Inventor: Jung Taek Oh, Seoul (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 799 days.

(21) Appl. No.: 14/559,434

(22) Filed: Dec. 3, 2014

(65) Prior Publication Data
US 2015/0190115 A1 Jul. 9, 2015

(30) Foreign Application Priority Data

Jan. 7, 2014 (KR) .......................... 10-2014-0002096

(51) Int. Cl.
*A61B 8/00* (2006.01)
*G10K 11/30* (2006.01)
*A61B 8/14* (2006.01)

(52) U.S. Cl.
CPC .......... *A61B 8/4444* (2013.01); *A61B 8/4405* (2013.01); *G10K 11/30* (2013.01); *A61B 8/14* (2013.01); *A61B 8/4411* (2013.01); *A61B 8/4433* (2013.01); *A61B 8/58* (2013.01)

(58) Field of Classification Search
CPC ... A61B 8/4444; A61B 8/4405; A61B 8/4433; A61B 8/4411; A61B 8/58; A61B 8/14; A61B 8/08
See application file for complete search history.

(56) References Cited

U.S. PATENT DOCUMENTS 5,471,988 A * 12/1995 Fujio .................. A61B 8/12
600/439
2004/0236217 A1* 11/2004 Cerwin ............... A61B 5/0073
600/437
2008/0281237 A1* 11/2008 Slayton ............... A61B 8/4281
601/2

FOREIGN PATENT DOCUMENTS

| JP | 2008-581 | 1/2008 |
| JP | 4932851 | 2/2012 |
| JP | 2012-50824 | 3/2012 |

* cited by examiner

*Primary Examiner* — Joel Lamprecht
(74) *Attorney, Agent, or Firm* — Staas & Halsey LLP

(57) ABSTRACT

An ultrasonic imaging device selectively obtains an accurate image of a target part inside an object or an image of a wide part inside the object through an ultrasonic probe by operating a focus adjustment unit. The ultrasonic imaging device includes an ultrasonic probe the front of which is equipped with a probe lens, and a focus adjustment unit mounted to the ultrasonic probe so as to selectively defocus the probe lens. The focus adjustment unit includes a focus adjustment portion arranged in the front of the probe lens, and a pressing portion connected to the focus adjustment portion so as to vary a curvature of the focus adjustment portion by external force.

21 Claims, 7 Drawing Sheets

ULTRASONIC IMAGING DEVICE

CROSS-REFERENCE TO RELATED APPLICATIONS

This application claims the priority benefit of Korean Patent Application No. 10-2014-0002096, filed on Jan. 7, 2014 in the Korean Intellectual Property Office, the disclosure of which is incorporated herein by reference.

BACKGROUND

1. Field

Embodiments disclosed herein relate to an ultrasonic imaging device.

2. Description of the Related Art

An ultrasonic imaging device generally refers to a device which projects ultrasonic waves from a surface of an object toward a target part inside the object and noninvasively obtains an image related to a monolayer or blood stream of soft tissue using information of ultrasonic signals (e.g., ultrasonic echo signals) reflected therefrom.

Such an ultrasonic imaging device may be small, cheap, and display a diagnostic image in real time, compared to other diagnostic imaging devices such as an X-ray diagnostic device, an X-ray CT scanner (X-ray computerized tomography scanner), an MRI (magnetic resonance image) device, and a nuclear medicine diagnostic device. Furthermore, since the ultrasonic imaging device does not cause radiation exposure, the ultrasonic imaging device is inherently safe. Accordingly, the ultrasonic imaging device is widely utilized for a variety of operations or procedures, including for example, cardiac, abdominal, urological, and maternity diagnosis.

SUMMARY

Therefore, it is an aspect of the disclosure to provide an ultrasonic imaging device capable of (configured to, suitable for, operable to, arranged to, adapted to, etc.) allowing a lens provided on an ultrasonic probe to be focused or defocused.

Additional aspects of the disclosure will be set forth in part in the description which follows and, in part, will be apparent from the description, or may be learned by practice of the disclosure.

In accordance with an aspect of the disclosure, an ultrasonic imaging device may include an ultrasonic probe the front of which may be equipped with a probe lens, and a focus adjustment unit mounted to the ultrasonic probe so as to be capable of (configured to, suitable for, operable to, arranged to, adapted to, etc.) selectively defocusing the probe lens. For example, the focus adjustment unit may include a focus adjustment portion arranged in the front of the probe lens, and a pressing portion connected to the focus adjustment portion so as to vary a curvature of the focus adjustment portion by application of an external force to the pressing portion.

When the curvature of the focus adjustment portion is varied by applying the external force to the pressing portion, the probe lens may be defocused.

The focus adjustment portion may be provided to be flat in an initial state in which the external force is not applied to the pressing portion.

When the speed of sound passing through the focus adjustment portion is slower than the speed of sound passing through water, the curvature of the focus adjustment portion may be varied such that the focus adjustment portion is formed in the form of a concave lens when the external force is applied to the pressing portion.

When the speed of sound passing through the focus adjustment portion is faster than the speed of sound passing through water, the curvature of the focus adjustment portion may be varied such that the focus adjustment portion is formed in the form of a convex lens when the external force is applied to the pressing portion.

The focus adjustment portion may be made of a flexible silicone rubber material.

The focus adjustment unit may further include an elastic member to provide elastic force to the pressing portion, and when the external force applied to the pressing portion is removed, the pressing portion may be returned to a state before applying the external force thereto by the elastic force.

When the external force applied to the pressing portion is removed, the focus adjustment portion may be returned to a state before the curvature thereof is varied.

The focus adjustment unit may include a mounting holder which is equipped, at one side thereof, with the pressing portion and is mounted to the ultrasonic probe.

The mounting holder may be formed with a hole into which the ultrasonic probe is inserted.

The mounting holder may be detachably mounted to the ultrasonic probe.

The pressing portion may include a first arm and a second arm to which the focus adjustment portion is mounted at one sides thereof.

The first and second arms may be provided to intersect with each other.

When the other side of the first arm is pressed in a direction of being close to the second arm or the other side of the second arm is pressed in a direction of being close to the first arm, the curvature of the focus adjustment portion may be varied.

When the curvature of the focus adjustment portion is varied by the external force applied to the pressing portion, a visible area of the ultrasonic probe may be widened compared to a state before the external force is applied to the pressing portion.

In accordance with another aspect of the disclosure, an ultrasonic imaging device may include an ultrasonic probe which generates ultrasonic waves to obtain an ultrasonic image of an object, and a focus adjustment portion which is provided in the front of the ultrasonic probe and is provided such that a curvature of the focus adjustment portion is capable of (configured to, suitable for, operable to, arranged to, adapted to, etc.) being varied by external force, wherein a visible area of the ultrasonic probe is varied according to the curvature of the focus adjustment portion.

The focus adjustment portion may be detachably provided to the ultrasonic probe.

The focus adjustment portion may be connected to a pressing portion, and when the external force is applied to the pressing portion, the curvature of the focus adjustment portion may be varied.

The pressing may be equipped with an elastic member, and when the external force applied to the pressing portion is removed, the pressing portion may be returned to a state before applying the external force thereto.

The front of the ultrasonic probe may be provided with a probe lens and the focus adjustment portion may be made of the same material as the probe lens.

In accordance with another aspect of the disclosure, an ultrasonic imaging device may include an ultrasonic probe to generate ultrasonic waves which pass through a probe lens of the ultrasonic probe to obtain an image of an object, and a focus adjustment unit connected to the ultrasonic probe to change a focus of the probe lens. The focus adjustment unit may include a focus adjustment portion provided at a front side of the probe lens which is selectively shaped according to whether the probe lens is to be maintained in a focused or defocused state.

The focus adjustment unit may further include a pressing portion connected to an upper surface of the focus adjustment portion to change a curvature of the focus adjustment portion.

The focus adjustment unit may further include a mounting holder having a hollow space on a top portion thereof into which the front side of the probe lens is inserted, and the pressing portion may include a first pair of intersecting arms disposed on an outer first side surface of the mounting holder, connected to a surface of the focus adjustment portion facing the probe lens, and a second pair of intersecting arms disposed on an outer second side surface of the mounting holder, connected to the surface of the focus adjustment portion facing the probe lens.

Rotation of the first pair and second pair of intersecting arms may change the curvature of the focus adjustment portion to maintain the probe lens in a focused or defocused state.

The shape of the focus adjustment portion may be changed according to whether a speed of sound passing through the probe lens is slower or faster than the speed of sound passing through water.

BRIEF DESCRIPTION OF THE DRAWINGS

These and/or other aspects of the disclosure will become apparent and more readily appreciated from the following description of the embodiments, taken in conjunction with the accompanying drawings of which.

DETAILED DESCRIPTION

Reference will now be made in detail to an ultrasonic imaging device according to example embodiments of the disclosure, the examples of which are illustrated in the accompanying drawings, wherein like reference numerals refer to like elements throughout.

Figure 1:
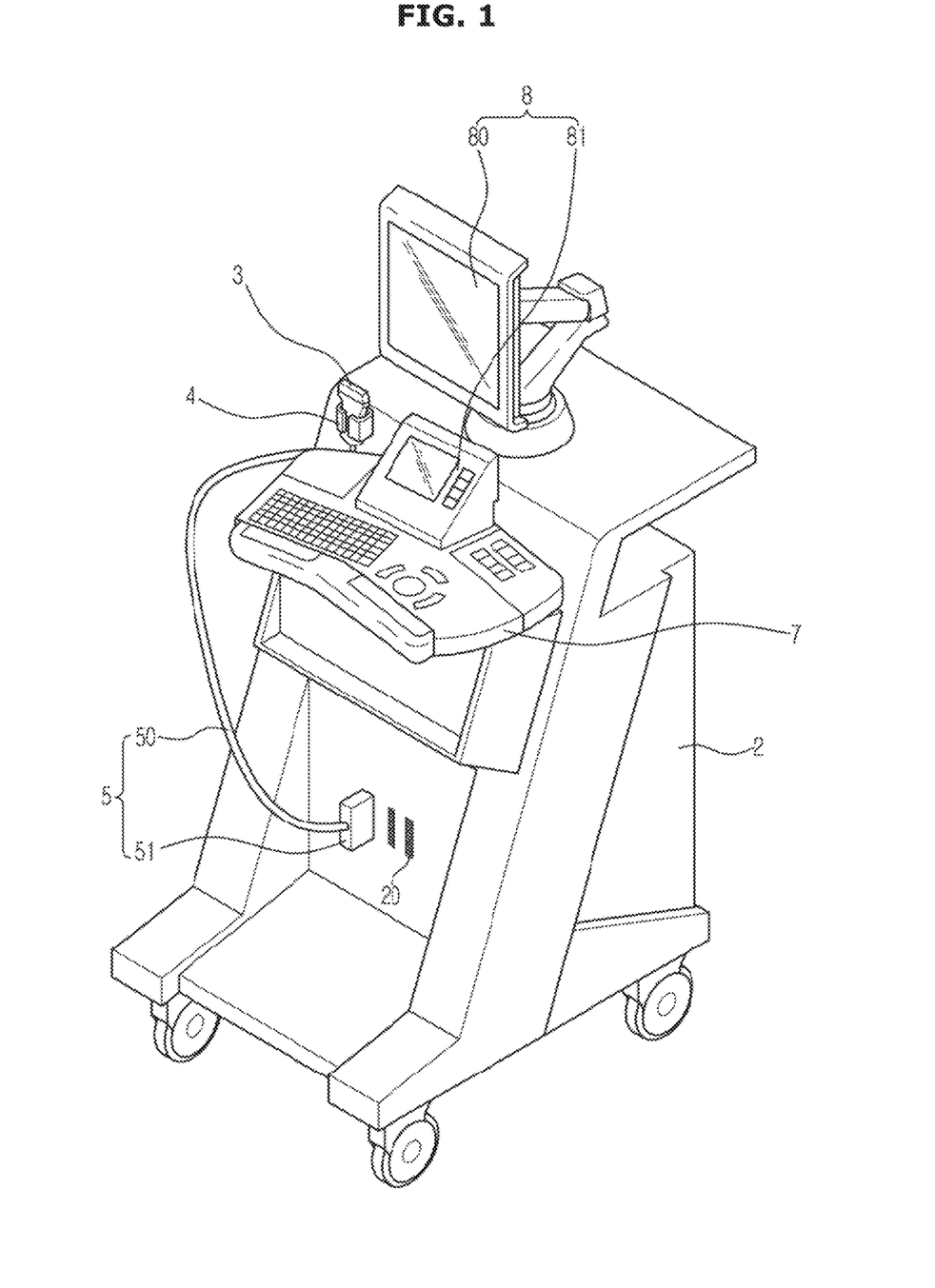
FIG. 1 is a view illustrating an ultrasonic imaging device according to an embodiment of the disclosure.

FIG. 1 is a view illustrating an ultrasonic imaging device according to an embodiment of the disclosure.

Referring to FIG. 1, the ultrasonic imaging device 1 according to an embodiment of the disclosure may include a main body 2, an ultrasonic probe 3, an input portion 7, and a display 8. The display 8 may include a main display 80 and a sub-display 81. The main body 2 may further include the input portion 7. For example, the input portion 7 may be integrated with the main body 2, and/or the input portion 7 may be remotely disposed or separate from the main body 2.

The display 8 may display an ultrasonic image obtained from an ultrasonic diagnostic process. In addition, the display 8 may display an application related to operation of the ultrasonic imaging device 1. For example, the main display 80 may display the ultrasonic image obtained from the ultrasonic diagnostic process. The sub-display 81 may display the application related to operation of the ultrasonic imaging device 1. In FIG. 1, the main display 80 and the sub-display 81 are provided. However, the disclosure is not so limited. The display 8 may include more than two displays, or may include only one display, for example.

The main display 80 and/or the sub-display 81 may be embodied by a CRT (Cathode-Ray Tube), an LCD (Liquid Crystal Display), and the like. The main display 80 or the sub-display 81 may be provided so as to be coupled to (integrated with) and/or separated (remotely disposed) from the main body 2. Other examples of the display may include a light emitting diode (LED) display, an organic light emitting diode (OLED) display, active matrix organic light emitting diode (AMOLED), flexible display, 3D display, a plasma display panel (PDP), and the like, for example. However, the disclosure is not limited to these example displays and may include other types of displays.

The main body 2 may include the input portion 7. The input portion 7 may be provided in the form of a foot switch or a foot pedal. When the input portion 7 is a keyboard, the input portion 7 may be arranged at an upper portion of the main body 2. When the input portion 7 is a foot switch or a foot pedal, the input portion 7 may be arranged at a lower portion of the main body 2. The operation of the ultrasonic imaging device 1 may be controlled through the input portion 7 by a user (e.g., a tester, operator, medical professional, etc.). It is noted input portion 7 may include one or a plurality of input portions. For example, an input portion may include a keyboard provided at an upper portion of the main body, and a foot pedal provided at a lower portion of the main body. Additional devices may be included as part of the input portion (e.g., a touch screen, a smart phone, a microphone, a mouse, etc.) For example, the input portion may also include one or more of a joystick, a button, a switch, an electronic pen or stylus, a gesture recognition sensor (e.g., to recognize gestures of a user including movements of a body part), an input sound device or voice recognition sensor (e.g., a microphone to receive a voice command), an output sound device (e.g., a speaker), a track ball, a remote controller, a portable (e.g., a cellular or smart) phone, a tablet PC, a virtual-reality device, and so on. The input portion may further include a haptic device to provide haptic feedback to a user. The input portion may also include a touch screen, for example.

The ultrasonic probe 3 may be connected to the main body 2 by a connection member 5. The connection member 5 may include a cable 50 and a connector 51. One side of the cable 50 may be provided with the ultrasonic probe 3 and the other side thereof may be provided with the connector 51. The connector 51 may be detachably mounted to a connection portion 20 provided in the main body 2. Consequently, the ultrasonic probe 3 may be connected to the main body 2.

The ultrasonic probe 3 may be connected to the main body 2 and may be held or secured to the main body 2 by a holder 4. When the ultrasonic imaging device is not used, a user (e.g., a tester, operator, medical professional, etc.) may store the ultrasonic probe 3 by holding (storing) the same in the holder 4.

Figure 2:
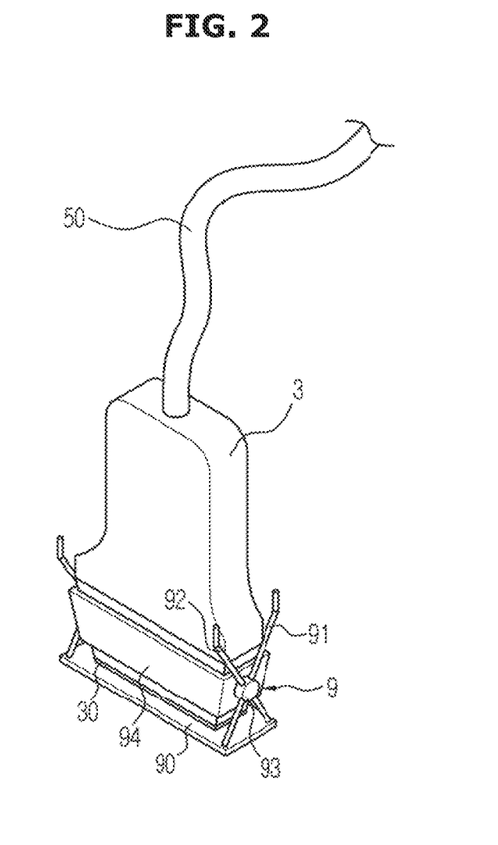
FIG. 2 is a view illustrating an ultrasonic probe equipped with a focus adjustment unit according to an embodiment of the disclosure.
Figure 3:
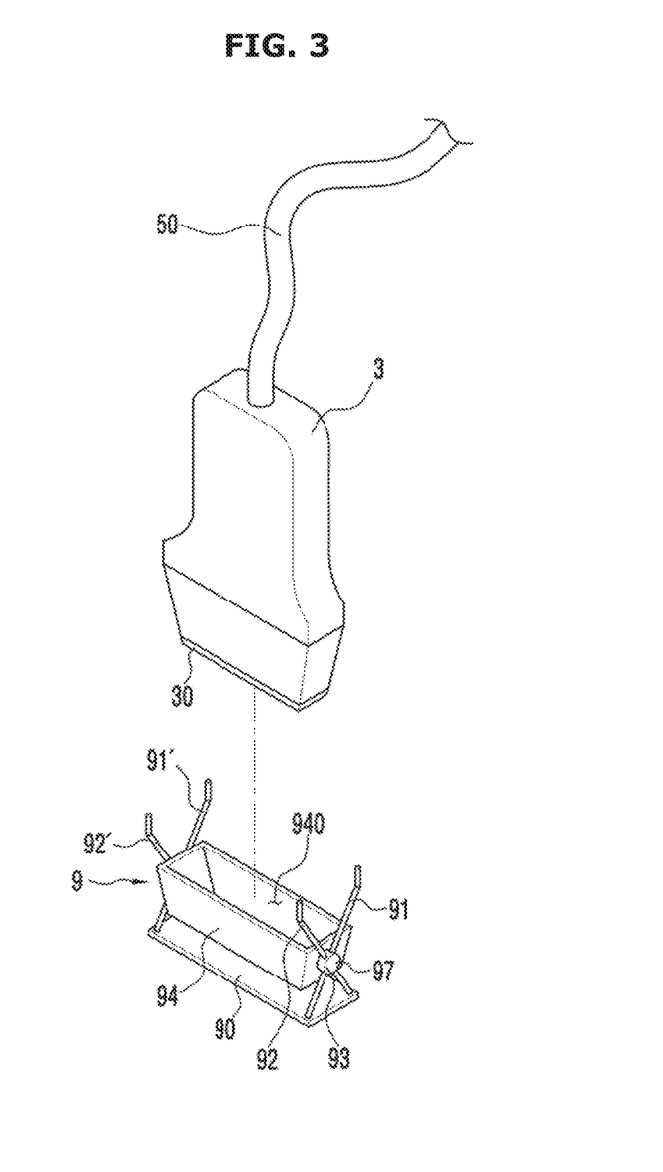
FIG. 3 is a view illustrating a separated state of the focus adjustment unit from the ultrasonic probe according to an embodiment of the disclosure.

FIG. 2 is a view illustrating the ultrasonic probe equipped with a focus adjustment unit according to an embodiment of the disclosure. FIG. 3 is a view illustrating a separated state of the focus adjustment unit from the ultrasonic probe according to an embodiment of the disclosure.

Referring to FIGS. 2 and 3, the ultrasonic probe 3 according to an embodiment of the disclosure may be equipped with the focus adjustment unit 9. A visible area of the ultrasonic probe 3 may be selectively widened by the focus adjustment unit 9. When the visible area of the ultrasonic probe 3 is widened by the focus adjustment unit 9, the ultrasonic probe 3 may be out of focus. This may be a defocused state. That is, when the ultrasonic probe 3 is defocused by the focus adjustment unit 9, it may be possible to obtain an image of a wider part inside an object compared to an image obtained in a focused state.

The ultrasonic probe 3 may include a piezoelectric layer, a matching layer provided on one side of the piezoelectric layer, a backing layer provided on the other side of the piezoelectric layer, and a probe lens 30 installed on one side of the matching layer.

When mechanical pressure is applied to a certain material, voltage is generated such that current may flow in the material. This is referred to as a piezoelectric effect. On the contrary, when a high voltage is applied to a material, mechanical deformation may be caused in the material. This may be referred to as an inverse piezoelectric effect. The material having such a piezoelectric effect or inverse piezoelectric effect may be referred to as a piezoelectric material. The piezoelectric material refers to a material which converts electric energy into mechanical vibration energy and vice versa.

The ultrasonic probe 3 typically may include the piezoelectric layer which receives electrical signals and converts the electrical signals into mechanical vibration so as to generate ultrasonic waves. The piezoelectric material composing the piezoelectric layer may include, for example, a PZT (lead zirconate titanate) ceramic, a PZMT single crystal made of a solid solution of lead magnesium niobate and lead titanate, a PZNT single crystal made of a solid solution of lead zinc niobate and lead titanate, or the like.

The matching layer may be provided on one surface of the piezoelectric layer. The matching layer may reduce an acoustic impedance difference between the piezoelectric layer and the object such that ultrasonic waves generated by the piezoelectric layer may be effectively transferred to the object.

The backing layer may be provided on the other surface of the piezoelectric layer. The backing layer may block ultrasonic waves generated by the piezoelectric layer from moving to a lower surface of the piezoelectric layer by absorbing the ultrasonic waves, thereby preventing image distortion. The backing layer may be provided in plural layers in order to improve attenuation and blocking effects of the ultrasonic waves.

The probe lens 30 may be provided on one surface of the matching layer. For example, the probe lens 30 may be made of a silicone rubber material. The probe lens 30 may be provided in a flat form. The probe lens 30 may also be formed in the form of a convex lens or a concave lens according to the speed of sound passing through the probe lens 30 in order to focus ultrasonic waves. That is, the probe lens 30 may be formed in the form of a convex lens or a concave lens based upon whether the speed of sound passing through the probe lens 30 is greater than a predetermined threshold. For example, the predetermined threshold may correspond to the speed of sound through water.

Generally, ultrasound waves travel at the speed of sound, where the speed of sound travelling through a material may depend on characteristics of the material (e.g., the density of the material, the compressibility of the material, etc.) For example, when the speed of sound passing through the probe lens 30 is slower than the speed of sound passing through water, the lens 30 may be formed in the form of the concave lens. For example, when the speed of sound passing through the probe lens 30 is faster than the speed of sound passing through water, the lens 30 may be formed in the form of the convex lens. As is known, the speed of sound passing through water is about 1480 m/s.

In order to obtain an internal image of the object, it may be possible to apply a medium similar to the object on the object and bring the probe lens 30 into contact with the object. Ultrasonic waves generated by the ultrasonic probe 3 may pass through the object via the ultrasonic lens 30 and then be reflected when the ultrasonic waves reach a part having a different medium inside the object. The reflected waves may be received by the ultrasonic probe 3 so as to be converted into image signals. The converted image signals may be displayed on the display 8.

The ultrasonic probe 3 may be equipped with the focus adjustment unit 9. The focus adjustment unit 9 may include a focus adjustment portion 90, a first arm 91, and a second arm 92. The focus adjustment portion 90 may be arranged at one-side ends of the first and second arms 91 and 92. The focus adjustment unit 9 may further include a mounting holder 94 which may be mounted to the ultrasonic probe 3.

The mounting holder 94 may be mounted on an outer peripheral surface of the ultrasonic probe 3. The mounting holder 94 may be provided to be fitted onto the outer peripheral surface of the ultrasonic probe 3. The mounting holder 94 may be formed with a hole 940 into which the ultrasonic probe 3 is fitted or inserted. An inner side surface of the mounting holder 94 having the hole 940 may be formed to correspond to the outer peripheral surface of the ultrasonic probe 3. The mounting holder 94 may be fitted onto the outer peripheral surface of the ultrasonic probe 3 so as to be fixed thereto. The mounting holder 94 or the ultrasonic probe 3 may be provided with a separate fixing unit which fixes the mounting holder 94 to the ultrasonic probe 3.

Figure 4:
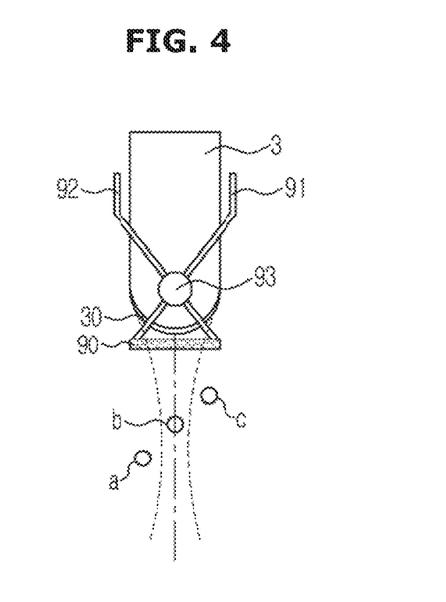
FIG. 4 is a view illustrating a state in which the ultrasonic probe is focused by the focus adjustment unit according to an embodiment of the disclosure.
Figure 6:
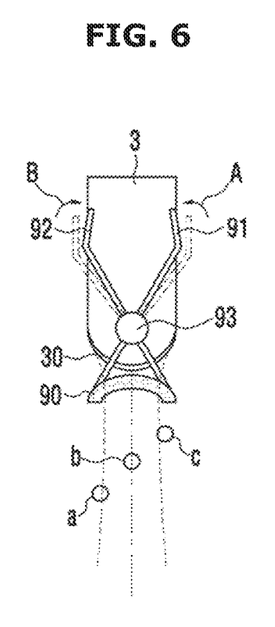
FIG. 6 is a view illustrating a state in which the ultrasonic probe is defocused by the focus adjustment unit according to an embodiment of the disclosure.

Each of the first and second arms 91 and 92 may be mounted to one side of the mounting holder 94. First and second arms 91' and 92' may be mounted to another side of the mounting holder 94. Alternatively, additional arms may be mounted to the mounting holder. The number of arms mounted to the mounting holder may depend on the size and/or shape of the mounting holder, for example. A connection portion 93 may be fixed to the mounting holder 94 and the first and second arms 91 and 92 may be connected to each other by intersecting about the connection portion 93. For example, the first and second arms 91 and 92 may intersect about the connection portion 93 so that one side of the first arm 91 may be located at a left lower end of the connection portion 93 and the other side thereof may be located at a right upper end of the connection portion 93 on the basis of the connection portion 93. One side of the second arm 92 may be located at a right lower end of the connection portion 93 and the other side thereof may be located at a left upper end of the connection portion 93. For example, the first and second arms may intersect about the connection portion so as to be substantially shaped in the form of an X. As shown in FIGS. 4 and 6, an upper portion of the first and second arms may be bent. For example, the bent portion of the first and second arms may be substantially parallel with a longitudinal axis of the ultrasonic probe.

The first and second arms 91 and 92 may be maintained in a state of forming a predetermined angle with each other by an elastic member 97. For example, the elastic member 97 may be a spring member which is mounted, at one side thereof, to the first arm 91 while being mounted, at the other side thereof, to the second arm 92. The elastic member 97 may apply elastic force such that one side or the other side of the first arm 91 is away from the second arm 92. The elastic member 97 may apply elastic force such that one side or the other side of the second arm 92 is away from the first arm 91. The elastic member 97 may be provided at the connection portion 93.

The focus adjustment portion 90 may be mounted to one side of the first arm 91 and one side of the second arm 92. The focus adjustment portion 90 may be made of the same material as the probe lens 30. Alternatively, the focus adjustment portion 90 may be made of a different material as the probe lens 30. For example, the focus adjustment portion 90 may be made of a flexible silicone rubber material. The first and second arms 91 and 92 may be mounted to the focus adjustment portion 90. The focus adjustment portion 90 may be arranged to be bent by operation of the first and second arms 91 and 92. The focus adjustment portion 90 may have a curvature thereof which is variable and may be varied by operation of the first and second arms 91 and 92.

The first and second arms 91 and 92 may be respectively provided on facing outer side surfaces of the mounting holder 94 such that the focus adjustment portion 90 is fixed at both sides thereof. For example, first and second arms 91 and 92 may be provided on one outer side surface of the mounting holder 94, and first and second arms 91' and 92 may be provided on another outer side surface of the mounting holder 94 which is opposite of the one outer side surface. For example, the focus adjustment portion 90 may be provided in a shape corresponding to the shape of the probe lens 30. For example, the focus adjustment portion 90 may have a size which is equal to or more than that of the probe lens 30. For example, the front side of the probe lens 30 may have an area which is equal to or less than an area of the focus adjustment portion 90.

The focus adjustment portion 90 may be flat in an initial state in which an external force is not applied to the first or second arm. In this case, the first and second arms 91 and 92 may form a predetermined angle with each other by the elastic member. When one side or the other side of the first arm 91 is close to the second arm 92 and one side or the other side of the second arm 92 is close to the first arm 91 by applying external force to the first or second arm 91 or 92 (e.g., by a user, tester, an operator, medical professional, etc.) the curvature of the focus adjustment portion 90 may be varied such that the focus adjustment portion 90 may be bent in the form of the convex lens or concave lens. Therefore, the first and second arms 91 and 92 may be referred to as a pressing portion.

When the external force applied to the first or second arm 91 or 92 is removed, the first or second arm 91 or 92 may be returned to an original position by moving in a direction in which one side or the other side of the first arm 91 is away from the second arm 92 and one side or the other side of the second arm 92 is away from the first arm 91 by elastic force of the elastic member. When the first or second arm 91 or 92 is returned to the original position, the focus adjustment portion 90 may be restored to the flat form of an initial state.

According to another example, the focus adjustment portion 90 may be provided to be bent in the form of the convex lens or concave lens when external force is not applied to the first or second arm, or the focus adjustment portion 90 may be provided to be flat when the user (e.g., a tester, operator, medical professional, etc.) applies external force to the first or second arm 91 or 92.

Hereinafter, a description will be given of an embodiment in which the focus adjustment portion 90 is provided to be flat when an external force is applied to the first or second arm 91 or 92 or the focus adjustment portion 90 is provided to be bent in the form of the convex lens or concave lens when the user (e.g., a tester, operator, medical professional, etc.) applies an external force to the first or second arm 91 or 92.

Figure 5:
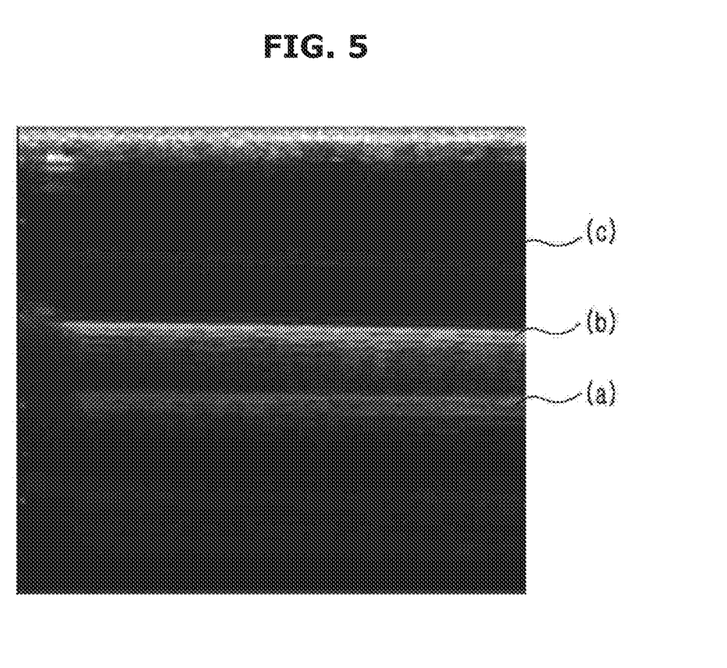
FIG. 5 is a view illustrating a focused image of the ultrasonic probe according to an embodiment of the disclosure.
Figure 7:
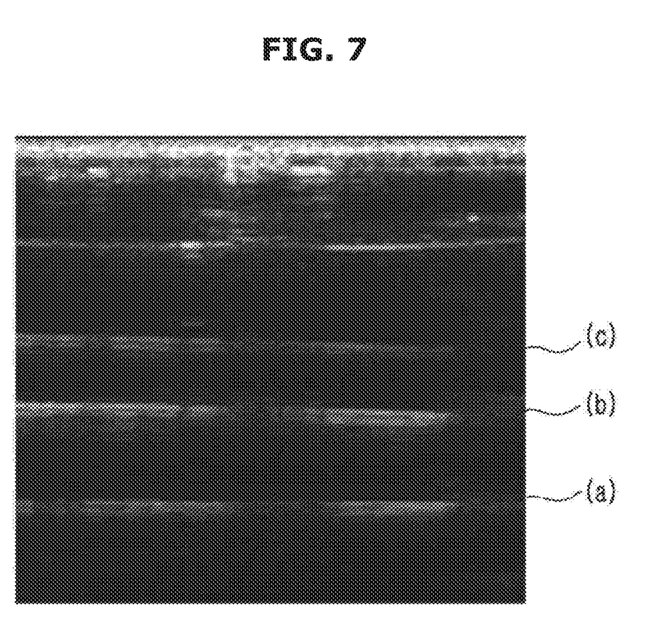
FIG. 7 is a view illustrating a defocused image of the ultrasonic probe according to an embodiment of the disclosure.

FIG. 4 is a view illustrating a state in which the ultrasonic probe is focused by the focus adjustment unit according to an embodiment of the disclosure. FIG. 5 is a view illustrating a focused image of the ultrasonic probe according to an embodiment of the disclosure. FIG. 6 is a view illustrating a state in which the ultrasonic probe is defocused by the focus adjustment unit according to an embodiment of the disclosure. FIG. 7 is a view illustrating a defocused image of the ultrasonic probe according to an embodiment of the disclosure.

Referring to FIGS. 4 to 7, the focus adjustment portion 90 according to an embodiment of the disclosure may be arranged forward of the probe lens 30 such that the probe lens 30 may be maintained in a focused state or may be in a defocused state.

In an initial state in which an external force is not applied to the first or second arm 91 or 92, the focus adjustment portion 90 may be arranged in a flat form in front of the probe lens 30. In this case, the focus adjustment portion 90 may not change the focus of the probe lens 30. That is, when the focus adjustment portion 90 is arranged forward of the probe lens 30 in the flat form, the probe lens 30 may be maintained in a focused state. Accordingly, it may be possible to obtain an accurate image of a specific area inside the object by the ultrasonic probe 3.

Assuming that a, b, and c points are forwardly spaced apart from the focus adjustment portion 90 as shown in FIG. 4, an image of the b point focused by the probe lens 30 may be obtained. Since the a and c points located at the left and right of the b point deviate from the focus area of the probe lens 30 as shown in FIG. 4, images of the a and c points may be not obtained or be defocused as shown in FIG. 5.

When the user (e.g., a tester, operator, medical professional, etc.) forces one end of the first arm 91 in an A direction (e.g., a counterclockwise direction) or one end of the second arm 92 in a B direction (e.g., a clockwise direction) as shown in FIG. 6, the focus adjustment portion 90 may be bent. For example, the focus adjustment portion 90 may be bent such that a central portion thereof is directed to the rear at which the probe lens 30 is located and edges thereof are directed to the front. The focus adjustment portion 90 may be bent in the form of the concave lens. That is, the central portion of the focus adjustment portion 90 may be drawn in toward the probe lens 30 and the outer portions of the focus adjustment portion 90 may be moved away from the probe lens 30.

When the focus adjustment portion 90 is bent, the probe lens 30 may be defocused. When the probe lens 30 is defocused, a visible area of the probe lens 30 may be widened. An image of a wider part inside the object may be obtained compared to an image obtained in the focused state by the probe lens 30. However, the obtained image may be defocused compared to an image in the focused state of the probe lens 30.

FIG. 6 shows that a, b, and c points are indicated at the same positions as FIG. 4. When the focus adjustment portion 90 is bent (e.g., in the form of a concave or convex lens) and the probe lens 30 is defocused, an image of a wide area may be obtained. As shown in FIGS. 6 and 7, the visible area of the probe lens 30 may be widened to the areas of the a and c points located at the left and right of the b point as well as the area of the b point. Thus, images of the a, b, and c points may be wholly obtained by the ultrasonic probe 3, for example as shown in FIG. 7. The image of the b point may be more defocused compared to a focused case of the probe lens 30.

In a case of requiring an accurate image of a specific part inside the object, the operator may obtain the ultrasonic image of the specific part inside the object using the ultrasonic probe 3 in a state of not operating the focus adjustment unit 9. In a case of requiring a general image of a wider area via the ultrasonic probe 3, the user (e.g., a tester, operator, medical professional, etc.) may allow the focus adjustment portion 90 to be bent by applying an external force to the focus adjustment unit 9. In a case of operating the inside of the object while viewing the ultrasonic image, the operator may obtain the general image of the wide area inside the object by operating the focus adjustment unit 9 at the user's (e.g., the tester's, operator's, medical professional's, etc.) convenience. The user (e.g., a tester, operator, medical professional, etc.) may be enabled or assisted to identify a position of a medical appliance such as an injection needle through the general image of the wide area inside the object.

While the above described example embodiments have described the case in which the focus adjustment portion 90 is deformed in the form of the concave lens, the focus adjustment portion 90 may also be bent in the form of the convex lens such that the central portion of the focus adjustment portion 90 is directed to the front and the edges thereof are directed to the rear by application of an external force. That is, the central portion of the focus adjustment portion 90 may be moved away from the probe lens 30 and the outer portions of the focus adjustment portion 90 may be drawn toward the probe lens 30. When the speed of sound passing through the focus adjustment portion 90 is slower than the speed of sound passing through water, the focus adjustment portion 90 may be deformed in the form of the concave lens by external force. When the speed of sound passing through the focus adjustment portion 90 is faster than the speed of sound passing through water, the focus adjustment portion 90 may be deformed in the form of the convex lens by external force. When the focus adjustment portion 90 is deformed in the form of the convex lens, the probe lens 30 may be defocused and the image of the wider area may be obtained by the probe lens 30.

As described above, it may be possible to selectively obtain an accurate image of a certain part inside the object or an image of a wide area inside the object through the probe lens 30 according to an operation of the focus adjustment portion 90 by the user (e.g., a tester, operator, medical professional, etc.). In a case of operating inside of the object using another medical appliance while viewing tissue inside the object using the ultrasonic imaging device 1, the user (e.g., a tester, operator, medical professional, etc.) may selectively operate the focus adjustment portion 90 in order to identify a position of the medical appliance being utilized as the occasion demands, thereby enabling an image of a wide area inside the object to be obtained or enabling an accurate image of an operated target part inside the object to be obtained.

The focus adjustment unit 9 may be detachably mounted to the ultrasonic probe 3. Therefore, the focus adjustment unit 9 may be decoupled from the ultrasonic probe 3 when focus adjustment is not required.

As is apparent from the above description, in accordance with an ultrasonic imaging device according to example embodiments of the disclosure, it may be possible to selectively obtain an accurate image of a target part inside an object or an image of a wide part inside the object through an ultrasonic probe by operating a focus adjustment unit.

Although example embodiments of the disclosure have been shown and described, it would be appreciated by those skilled in the art that changes may be made to these embodiments without departing from the principles and spirit of the disclosure, the scope of which is defined in the claims and their equivalents.

What is claimed is:

1. An ultrasonic imaging device comprising:
an ultrasonic probe which has a front side equipped with a probe lens; and
a focus adjustment unit mounted to the ultrasonic probe to selectively defocus the probe lens,
wherein the focus adjustment unit comprises:
a mounting holder mounted on an outer surface of the ultrasonic probe;
a focus adjustment portion arranged at a front side of the probe lens and spaced apart a predetermined distance from the mounting holder;
a pressing portion connected to the focus adjustment portion to vary a curvature of the focus adjustment portion when an external force is applied to the pressing portion; and
an elastic member to provide an elastic force to the pressing portion, and when the external force applied to the pressing portion is removed, the pressing portion is returned to a state before applying the external force thereto by the elastic force.

2. The ultrasonic imaging device according to claim 1, wherein when the curvature of the focus adjustment portion is varied by applying the external force to the pressing portion, the probe lens is defocused.

3. The ultrasonic imaging device according to claim 1, wherein the focus adjustment portion is provided to be flat in an initial state in which the external force is not applied to the pressing portion.

4. The ultrasonic imaging device according to claim 1, wherein when a speed of sound passing through the focus adjustment portion is slower than the speed of sound passing through water, the curvature of the focus adjustment portion is varied such that the focus adjustment portion is formed in the form of a concave lens when the external force is applied to the pressing portion.

5. The ultrasonic imaging device according to claim 1, wherein when a speed of sound passing through the focus adjustment portion is faster than the speed of sound passing through water, the curvature of the focus adjustment portion is varied such that the focus adjustment portion is formed in the form of a convex lens when the external force is applied to the pressing portion.

6. The ultrasonic imaging device according to claim 1, wherein the focus adjustment portion is made of a flexible silicone rubber material.

7. The ultrasonic imaging device according to claim 1, wherein when the external force applied to the pressing portion is removed, the focus adjustment portion is returned to a state before the curvature thereof is varied.

8. The ultrasonic imaging device according to claim 1, wherein the mounting holder is equipped with the pressing portion on at least one side of the mounting unit.

9. The ultrasonic imaging device according to claim 8, wherein the mounting holder is formed with a hole into which the ultrasonic probe is inserted.

10. The ultrasonic imaging device according to claim 9, wherein the mounting holder is detachably mounted to the ultrasonic probe.

11. The ultrasonic imaging device according to claim 1, wherein the pressing portion comprises a first arm and a second arm to which the focus adjustment portion is mounted on at least one side thereof.

12. The ultrasonic imaging device according to claim 11, wherein the first and second arms are provided to intersect with each other.

13. The ultrasonic imaging device according to claim 12, wherein when one side of the first arm is pressed in a direction of being close to the second arm or when one side of the second arm is pressed in a direction of being close to the first arm, the curvature of the focus adjustment portion is varied.

14. The ultrasonic imaging device according to claim 1, wherein when the curvature of the focus adjustment portion is varied by the external force applied to the pressing portion, a visible area of the ultrasonic probe is widened compared to a state before the external force is applied to the pressing portion.

15. An ultrasonic imaging device comprising:
an ultrasonic probe which generates ultrasonic waves to obtain an ultrasonic image of an object; and
a focus adjustment portion which is provided at a front side of the ultrasonic probe and spaced apart in an outward direction a predetermined distance from the ultrasonic probe, and is provided such that a curvature of the focus adjustment portion is varied by application of an external force,
wherein a visible area of the ultrasonic probe is varied according to the curvature of the focus adjustment portion,
wherein the focus adjustment portion is connected to a pressing portion, and when the external force is applied to the pressing portion, the curvature of the focus adjustment portion is varied, and
wherein the pressing portion is equipped with an elastic member, and when the external force applied to the pressing portion is removed, the pressing portion is returned to a state before applying the external force thereto.

16. The ultrasonic imaging device according to claim 15, wherein the focus adjustment portion is detachably provided to the ultrasonic probe.

17. The ultrasonic imaging device according to claim 15, wherein the front side of the ultrasonic probe is provided with a probe lens and the focus adjustment portion is made of the same material as the probe lens.

18. An ultrasonic imaging device comprising:
an ultrasonic probe to generate ultrasonic waves which pass through a probe lens of the ultrasonic probe to obtain an image of an object; and
a focus adjustment unit connected to the ultrasonic probe to change a focus of the probe lens,
wherein the focus adjustment unit comprises:
a mounting holder having a hollow space in a top portion thereof into which a front side of the probe lens is inserted,
a focus adjustment portion provided at the front side of the probe lens and spaced apart a predetermined distance from the mounting holder, and which is selectively shaped according to whether the probe lens is to be maintained in a focused or defocused state;
a pressing portion connected to an upper surface of the focus adjustment portion to change a curvature of the focus adjustment portion; and
an elastic member to provide an elastic force to the pressing portion, and when an external force applied to the pressing portion is removed, the pressing portion is returned to a state before applying the external force thereto by the elastic force.

19. The ultrasonic imaging device according to claim 18, wherein
the pressing portion comprises:
a first pair of intersecting arms disposed on an outer first side surface of the mounting holder, connected to a surface of the focus adjustment portion facing the probe lens, and
a second pair of intersecting arms disposed on an outer second side surface of the mounting holder, connected to the surface of the focus adjustment portion facing the probe lens.

20. The ultrasonic imaging device according to claim 19, wherein rotation of the first pair and second pair of intersecting arms changes the curvature of the focus adjustment portion to maintain the probe lens in a focused or defocused state.

21. The ultrasonic imaging device according to claim 18, wherein a shape of the focus adjustment portion is changed according to whether a speed of sound passing through the probe lens is slower or faster than the speed of sound passing through water.

* * * * *